US00PP18413P2

(12) United States Plant Patent
Andrusiv

(10) Patent No.: US PP18,413 P2
(45) Date of Patent: Jan. 8, 2008

(54) ***BERBERIS* PLANT NAMED 'ROSY ROCKET'**

(50) Latin Name: *Berberis thunbergii*
Varietal Denomination: ROSY ROCKET

(76) Inventor: Michal Andrusiv, J Metyse 1079, Litomysl (CZ), 570 01

( * ) Notice: Subject to any disclaimer, the term of this patent is extended or adjusted under 35 U.S.C. 154(b) by 1 day.

(21) Appl. No.: 11/544,375

(22) Filed: Oct. 10, 2006

(51) Int. Cl.
*A01H 5/00* (2006.01)

(52) U.S. Cl. ..... Plt./241

(58) Field of Classification Search ..... Plt./241
See application file for complete search history.

*Primary Examiner*—Kent Bell

(57) ABSTRACT

A new cultivar of *Berberis* plant named 'ROSY ROCKET' that is characterized by an upright columnar habit and red foliage. In combination these traits set 'ROSY ROCKET' apart from all other existing varieties of *Berberis* known to the inventor.

1 Drawing Sheet

Genus: *Berberis*. Species: *thunbergii*.
Denomination: 'ROSY ROCKET'.

BACKGROUND OF THE INVENTION

The present invention relates to a new and distinct cultivar of barberry that is grown as a dwarf shrub for container or landscape. The new cultivar is known botanically as *Berberis thunbergii* and will be referred to hereinafter by the cultivar name 'ROSY ROCKET'.

'ROSY ROCKET' was selected by the inventor in Litomysl, The Czech Republic in 1994, for unique foliage color. The new cultivar 'ROSY ROCKET' is a hybrid plant that resulted from cross-pollination conducted by the inventor in a cultivated area of Litomysl, The Czech Republic. Cross-pollination was between an individual plant of seed parent *Berberis thunbergii* 'Aurea' (unpatented) and an individual plant of pollen parent *Berberis thunbergii* 'Helmond Pillar' (unpatented).

The new *Berberis* variety 'ROSY ROCKET' is a deciduous dwarf shrub characterized by red foliage. This foliage color continues throughout the summer season. The height of the plant is three times its width. The foliage color and plant habit distinguish 'ROSY ROCKET' from all other *Berberis* known to the inventor.

The new *Berberis* variety 'ROSY ROCKET' differs from the yellow foliaged female parent plant *Berberis thunbergii* 'Aurea' in that 'ROSY ROCKET' is columnar. The new *Berberis* variety 'ROSY ROCKET' differs from the purple foliaged male parent plant *Berberis thunbergii* 'Helmond Pillar' in that 'ROSY ROCKET' is red in color and slightly smaller in size. The closest variety of *Berberis thunbergii* known to the inventor is the male parent *Berberis thunbergii* 'Helmond Pillar' described above.

The first asexual reproduction of 'ROSY ROCKET' was conducted by the inventor in 1995 in a cultivated area of Litomysl, The Czech Republic. The method used for asexual propagation was vegetative cuttings. Since that time the distinguishing characteristics of 'ROSY ROCKET' have been determined stable and have reproduced true to type in successive generations of asexual reproduction.

The inventor filed an application for a grant of European Community Plant Breeder's Rights for 'ROSY ROCKET' on Sep. 22, 2005, Serial Number 2005/1759. During spring 2005, the inventor provided six plants of 'ROSY ROCKET' to The Royal Horticultural Society, England, for planting in the Society's secure trials area which is not on view nor accessible to the public. The first public showing and the first offer for sale of any plants of 'ROSY ROCKET' took place at the Plantarium exhibition in The Netherlands in August 2006, at which show 'ROSY ROCKET' was entered in the new plants competition and was awarded a Bronze Medal.

SUMMARY OF THE INVENTION

The following traits have been repeatedly observed and represent the characteristics of the new *Berberis* cultivar 'ROSY ROCKET'. These traits in combination distinguish 'ROSY ROCKET' from all other commercial varieties of *Berberis* known to the inventor. 'ROSY ROCKET' has not been tested under all possible conditions and phenotypic differences may be observed with variations in environmental, climatic and cultural conditions, without however, any variance in genotype.

1. *Berberis* 'ROSY ROCKET' is a deciduous shrub.
2. *Berberis* 'ROSY ROCKET' is suitable for use in containers or the landscape.
3. *Berberis* 'ROSY ROCKET' exhibits an upright, columnar habit.
4. *Berberis* 'ROSY ROCKET' exhibits red foliage.
5. *Berberis* 'ROSY ROCKET' is propagated using vegetative cuttings.
6. *Berberis* 'ROSY ROCKET' is hardy to USDA Zone 5.
7. After 10 years, *Berberis* 'ROSY ROCKET' achieves 120 cm in height and 40 cm in width.

BRIEF DESCRIPTION OF THE DRAWING

The accompanying color drawing.

BOTANICAL DESCRIPTION OF THE PLANT

Figure 1:
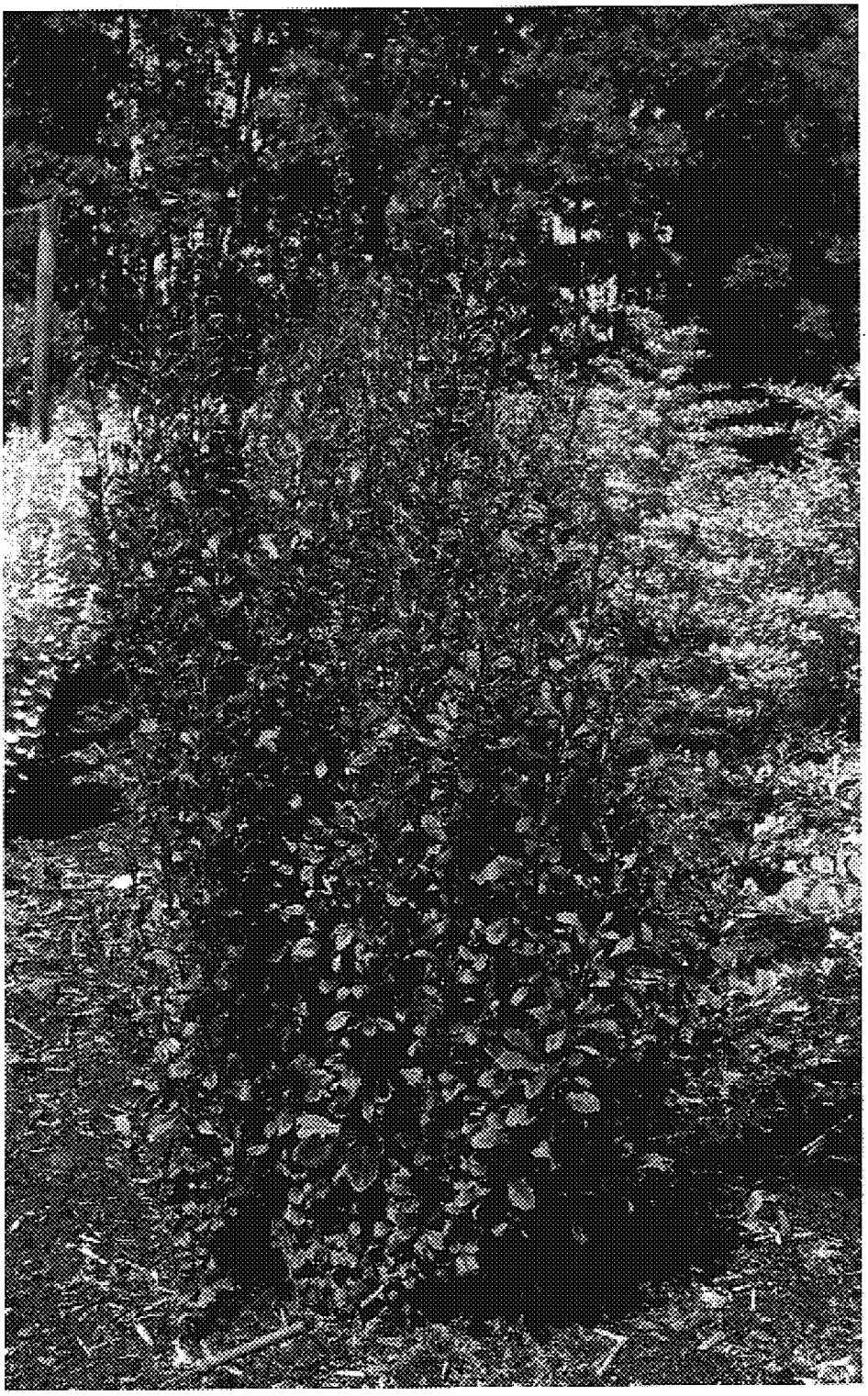
FIG. 1, illustrates the overall appearance of the new cultivar 'ROSY ROCKET' showing the colors as true as it is reasonably possible to obtain in colored reproductions of this type. The plant shown in the drawing is two-years-old grown out-of-doors in Boskoop, The Netherlands. The drawing illustrates the red foliage and upright habit of 'ROSY ROCKET'. Daytime temperatures averaged 15° Centigrade to 30° Centigrade. Nighttime temperatures ranged from −7° Centigrade to 14° Centigrade. The light was normal outdoor light level. No photoperiodic treatments and no growth retardants were applied to the plants. Colors in the drawing may differ from the color values cited in the detailed botanical description, which accurately describe the actual colors of the new variety of *Berberis* named 'ROSY ROCKET'. The drawing was made using conventional techniques and although colors may appear different from actual colors due to light reflectance they are as accurate as possible by conventional photography.

The following is a detailed description of 'ROSY ROCKET' as grown in a 2-liter containers, out-of-doors in Boskoop, The Netherlands. The observed plant was two years old. The color determinations are in accordance with the 2001 Edition of the Colour Chart of The Royal Horticultural Society except where general color terms of ordinary dictionary significance are used. The growing requirements are similar to the species.

Botanical classification:
- *Genus.*—*Berberis.*
- *Species.*—*thunbergii.*
- *Denomination.*—'ROSY ROCKET'.

Commercial classification: Deciduous shrub.

Use: Plant for use in containers or landscape.

Common name: Barberry.

Commercial container size: For liner production, a 5 cm round or square plug or cell or container; for planting in the garden or landscape, a 1 gallon or equivalent or larger container.

Cultural requirements: Plant in full sun to light shade in well-drained soil with moderate to regular water.

Parentage: *Berberis* 'ROSY ROCKET' is a hybrid plant that resulted from cross-pollination of the following parents:
- *Seed parent.*—*Berberis thunbergii* 'Aurea'.
- *Pollen parent.*—*Berberis thunbergii* 'Helmond Pillar'.

Plant description:
- *Bloom period.*—Beginning in spring.
- *Plant habit.*—Upright habit.
- *Overall plant shape.*—Columnar.
- *Vigor.*—Low.
- *Root system.*—Fibrous roots.
- *Plant dimensions.*—120 cm in height and 40 cm in width after 10 years.
- *Growth rate.*—Height increases by approximately 15 cm per year.
- *Hardiness.*—USDA Zone 4.
- *Propagation.*—Propagation is accomplished using stem tip or internodal cuttings.
- *Rooting time.*—An average of 6 weeks is needed for an initial cutting to develop roots.
- *Crop time.*—24 months are needed to produce a commercial 2-liter container from a rooted cutting.
- *Special growing considerations.*—Pinching back improves basal branching without loss of columnar habit.
- *Disease resistance and susceptibility.*—Not more susceptible to pests and diseases than other *Berberis thunbergii* cultivars known to the inventor. The United States Department of Agriculture, Agricultural Research Service Cereal Disease Laboratory completed testing and found the cultivar resistant to Wheat Stem Rust.

Stem:
- *Dimensions, main stem.*—30 cm in length and 2 mm in diameter.
- *Dimensions, secondary stem.*—29 mm to 40 mm in length and 1.5 mm in diameter.
- *Color, new growth.*—154A and N167B.
- *Color, mature growth.*—A mixture of 187A and 201A to 201D.
- *Surface.*—Rough.
- *Spines.*—Present.
- *Spine dimensions.*—7 mm in length.
- *Spine color.*—200B.
- *Spine arrangement.*—Singly and alternate.
- *Spine angle.*—90° on stem.

Foliage:
- *Type.*—Deciduous.
- *Arrangement.*—Borne in alternate clusters of 2 to 4.
- *Leaf division.*—Simple.
- *Leaf shape.*—Obovate to spatulate.
- *Leaf dimensions.*—19 mm to 35 mm in length to 8 mm to 13 mm in diameter.
- *Leaf apex.*—Obtuse to mucronate.
- *Leaf base.*—Attenuate.
- *Leaf venation pattern.*—One-veined from base.
- *Leaf margin type.*—Entire.
- *Leaf surface* (*adaxial and abaxial*).—Glabrous.
- *Color, mature leaf* (*adaxial*).—N77A and 178A.
- *Color, mature leaf* (*abaxial*).—146D to 147C.
- *Color, immature leaf* (*adaxial*).—60A to 60B and 183B (leaf is mottle variegated).
- *Color, immature leaf* (*abaxial*).—147B to 133B and 68A (upper surface mottling visible from below).
- *Attachment.*—Some sessile, some petiolate.
- *Petiole length.*—Where petiolate, length varies between 1 mm and 8 mm.

Flowers:
- *Inflorescence form.*—Axillary raceme, 2–4 flowers per raceme.
- *Number per stem.*—10–20 racemes per stem.
- *Time and duration of flowering.*—April–June.
- *Pedicel length.*—12 mm.
- *Dimensions.*—1 to 2 cm in diameter, 6 mm to 12 mm in depth.
- *Color.*—4C to 4D.
- *Fragrance.*—None.

Fruit: Borne singly or in clusters of 2–4 fruits at each node.
- *Number per stem.*—30–50.
- *Dimensions.*—1 cm–2 cm.
- *Cover.*—Fleshy.
- *Shape.*—Ellipsoid.
- *Firmness.*—Solid, juicy.
- *Color.*—43A, but brighter.

Seeds:
- *Quantity.*—1 or 2 per fruit.
- *Observed immature.*—Green, ellipsoid, 3 mm×2 mm.
- *Not observed mature but may be typical of species.*—Brown, concavo-convex, 3 mm×2 mm.

It is claimed:

1. A new and distinct cultivar of *Berberis* plant named 'ROSY ROCKET', as described and illustrated here within.

* * * * *